(12) United States Patent
Wang

(10) Patent No.: US 6,864,237 B2
(45) Date of Patent: Mar. 8, 2005

(54) TREATMENT OF SHOCK USING ADRENOMEDULLIN AND ADRENOMEDULLIN BINDING PROTEIN-1

(76) Inventor: Ping Wang, 3 Ridge Dr. East, Roslyn, NY (US) 11576

( * ) Notice: Subject to any disclaimer, the term of this patent is extended or adjusted under 35 U.S.C. 154(b) by 0 days.

(21) Appl. No.: 10/439,762

(22) Filed: May 16, 2003

(65) Prior Publication Data

US 2003/0216291 A1 Nov. 20, 2003

Related U.S. Application Data

(60) Provisional application No. 60/380,838, filed on May 17, 2002.

(51) Int. Cl.[7] ........................... A61K 38/00; C12N 9/00
(52) U.S. Cl. ........................................ 514/12; 435/183
(58) Field of Search ..................... 435/183; 424/94.1; 514/12

(56) References Cited

PUBLICATIONS

Fowler et al., "The cardiovascular response in sepsis: Proposed mechanisms of the beneficial effect of adrenomedullin and its binding protein (Review)", Apr. 17, 2002, 9, 443–449.*

Elsasser T.H. et al., "Adrenomedullin binding protein in the plasma of multiple species: characterization by radioligand blotting"; Endocrinol 140:4908–4911, 1999.

Shindo T. et al., "Hypotension and resistance to lipopolysaccharide–induced shock in transgenic mice overexpressing adrenomedullin in their vasculature"; Circulation 101:2309–2316, 2000.

Wichterman K.A. et al., "Sepsis and septic shock: a review of laboratory models and a proposal"; J Surg Res 29:189–201, 1980.

Wu R. et al., "Adrenomedullin and adrenomedullin binding protein–1 downregulate TNF–alpha in macrophage cell line and rat Kupffer cells"; Regul Pept 112:19–26, 2003.

Yang S et al., "Novel approach to prevent the transition from the hyperdynamic phase to the hypodynamic phase of sepsis: The role of adrenomedullin and adrenomedullin binding protein–1"; Crit Care Med. 29 (12, Suppl.) abst. A12, Dec. 2001.

Yang S. et al., "Novel approach to prevent the transition from the hyperdynamic phase to the hypodynamic phase of sepsis: Role of adrenomedullin and adrenomedullin binding protein–1"; Ann Surg 236:625–633, 2002.

Yang S. et al., "Mechanisms of the beneficial effect of adrenomedullin and adrenomedullin–binding protein–1 in sepsis: down–regulation of proinflammatory cytokines"; Crit Care Med 30:2729–2735, 2002.

* cited by examiner

Primary Examiner—Robert A. Wax
Assistant Examiner—Suzanne M. Mayer
(74) Attorney, Agent, or Firm—Amster, Rothstein & Ebenstein LLP

(57) ABSTRACT

The present invention provides methods of preventing organ destruction and shut-down due to shock in a patient suffering from sepsis or at risk for sepsis, comprising administering adrenomedullin and adrenomedullin binding protein-1 to the patient. Also provided are compositions containing adrenomedullin and adrenomedullin binding protein-1 or precursors, in a pharmaceutically acceptable carrier.

9 Claims, No Drawings

TREATMENT OF SHOCK USING ADRENOMEDULLIN AND ADRENOMEDULLIN BINDING PROTEIN-1

CROSS-REFERENCE TO RELATED APPLICATION

This application claims the benefit of U.S. Provisional Application No. 60/380,838, filed May 17, 2002, incorporated by reference in its entirety.

STATEMENT REGARDING FEDERALLY SPONSORED RESEARCH OR DEVELOPMENT

The research from which this invention resulted was supported by the United States Government, National Institutes of Health, grants RO1 GM57468 and KO2 A101461.

BACKGROUND OF THE INVENTION (1) Field of the Invention

This invention relates to treatment of shock to prevent organ shut-down during the hypodynamic phase. The invention described herein involves administration of adrenomedullin in conjunction with administration of adrenomedullin binding protein-1.

(2) Description of the Related Art

References Cited

Elsasser T H, Kahl S, Martinez A, Montuenga L M, Pio R, Cuttitta F: Adrenomedullin binding protein in the plasma of multiple species: characterization by radioligand blotting. *Endocrinol* 140:4908–4911, 1999.

Shindo T, Kurihara H, Maemura K, Kurihara Y, Kuwaki T, Izumida T, Minamino N, Ju K H, Morita H, Oh-hashi Y, Kumada M, Kangawa K, Nagai R, Yazaki Y: Hypotension and resistance to lipopolysaccharide-induced shock in transgenic mice overexpressing adrenomedullin in their vasculature. *Circulation* 101:2309–2316, 2000.

Wichterman K A, Baue A E, Chaudry I H: Sepsis and septic shock: a review of laboratory models and a proposal. *J Surg Res* 29:189–201, 1980.

Wu R, Zhou M, Wand P: Adrenomedullin and adrenomedullin binding protein-1 downregulate TNF-α in macrophage cell line and rat Kupffer cells. *Regul Pept* 112:19–26, 2003.

Yang S, Zhou M., Chaudry I H: Novel approach to prevent the transition from the hyperdynamic phase to the hypodynamic phase of sepsis: Role of adrenomedullin and adrendomedullin binding protein-1. *Ann Surg* 236:625–633, 2002a.

Yang S, Zhou M, Gowler D E, Wang P: Mechanisms of the beneficial effect of adrenomedullin and adrenomedullin-binding protein-1 in sepsis: down-regulation of proinflammatory cytokines. *Crit Care Med* 30:2729–2735, 2002b.

Despite attempts to improve survival of septic patients with intensive medical care, including antibiotics, aggressive intravenous fluids, nutrition, mechanical ventilation, and surgical interventions, the mortality rate still ranges from 30% to 50%. Of clinical trials testing novel agents for the treatment of sepsis, only activated protein C has previously been demonstrated to significantly reduce mortality in patients with severe sepsis. The high morbidity and mortality attributed to sepsis could be due to the fact that mediators or factors responsible for the transition from the hyperdynamic stage to the hypodynamic stage of sepsis are not fully understood. Consequently, there is a progressive deterioration of cell and organ functions and even death of the host, which might be prevented by interventions directed against and/or modulating these mediators/factors. It is therefore important to investigate the subtle alterations in cellular function and mechanisms of pathophysiological changes during sepsis and develop novel therapeutic strategies. In this regard, experimental polymicrobial sepsis induced by cecal ligation and puncture (CLP) mimics many features of clinical sepsis-peritonitis and is associated with an early, hyperdynamic phase (characterized by increased cardiac output and tissue perfusion, decreased vascular resistance, hyperglycemia and hyperinsulinemia) followed by a late, hypodynamic phase (characterized by reduced cardiac output and tissue perfusion, increased vascular resistance, hypoglycemia and hypoinsulinemia). The CLP model of sepsis has been used extensively to study the pathophysiologic and immunologic alterations in sepsis.

Adrenomedullin (AM), a newly reported and potent vasodilatory peptide, is an important mediator involved in both physiological and pathological states. The rat DNA sequence has been submitted to GenBank, accession number D15069. Human AM, a 52-amino acid peptide, was first isolated and reported in 1993. AM has a carboxy terminal amidated residue and a 6-member ring structure formed by an intramolecular disulfide bond near the amino terminus, and is available commercially. The complimentary DNA has been cloned and sequenced for both the human and rat form of AM. Rat AM has 50 amino acids with 2 amino acid deletions and 6 substitutions as compared to human AM. Adrenomedullin transcripts and protein are expressed in a large number of tissues, and circulating levels of AM were observed under normal as well as pathophysiological conditions. Previous studies using the CLP model of sepsis have shown that up-regulation of AM plays a major role in initiating the hyperdynamic response during the early stage of sepsis, and reduced vascular responsiveness to AM appears to be responsible for the transition from the hyperdynamic phase to the hypodynamic phase during the progression of polymicrobial sepsis.

In 1999, Elsasser et al. reported that specific AM binding proteins (AMBP) exist in the plasma of several species including humans. More recently, the binding protein (i.e., AMBP-1) has been identified in human plasma and has been shown to be identical to human complement factor H. The sequence data relating to this protein has been deposited in EMBL/GenBank Data Libraries under accession number Y00716. AMBP-1 enhances AM-mediated induction of cAMP in fibroblasts, augments the AM-mediated growth of a cancer cell line, and suppresses the bactericidal capability of AM on *E. coli*.

Studies by Shindo et al. have shown that a chronic increase in vascular AM production in transgenic mice was protective against circulatory collapse, organ damage, and mortality of endotoxic shock. It was previously unknown whether AM/AMBP-1 down-regulates proinflammatory cytokines and, if so, whether the beneficial effects of AM/AMBP-1 are due to this down-regulation.

It has been previously demonstrated that proinflammatory cytokines play a critical role in the initiation and progression of sepsis syndrome and that TNF-α, IL-1β and IL-6 are important mediators of hemodynamic, metabolic and immunologic alterations in the host during sepsis. Studies have also shown that circulating levels of TNF-α, IL-1β and IL-6 increase significantly in the early, hyperdynamic stage of sepsis and remain elevated in the late, hypodynamic stage of sepsis. Although AM is up-regulated following stimulation with TNF-α and IL-1β, some studies have shown that AM suppresses IL-1β-induced TNF-α production in vivo and suppresses the secretion of TNF-α and IL-6 from RAW 264.7 cells stimulated with endotoxin in vitro.

BRIEF SUMMARY OF THE INVENTION

The instant invention relates to means for treating shock by administration of adrenomedullin (AM) in conjunction with adrenomedullin binding protein-1 (AMBP-1) to prevent cardiovascular collapse and organ shut-down. Compositions containing AM and AMBP-1 given in conjunction with each other, either separately or in a composition containing both, protects from fatal outcomes from septic shock. Results indicate that administration of AM/AMBP-1 early after the onset of sepsis maintains cardiac output, organ perfusion, and systemic oxygen delivery at 20 h after CLP (i.e., the late stage of sepsis). Moreover, AM/AMBP-1 attenuates hepatocellular injury, lactic acidosis, and prevents the hemoconcentration under such conditions. Thus, AM/AMBP-1 is a novel approach to the treatment of sepsis. Since AM/AMBP-1 significantly reduced circulating levels of TNF-α, IL-1β and IL-6, down-regulation of those proinflammatory cytokines by AM/AMBP-1 appears to play an important role for the beneficial effects of these agents in polymicrobial sepsis.

DETAILED DESCRIPTION OF THE INVENTION

It is the purpose of this invention to provide means of preventing death resulting from shock. The invention relates most specifically to septic shock. It has now been found that administration of AM/AMBP-1 following the onset of sepsis (i.e., post-treatment and clinically relevant) has beneficial effects in maintaining cardiovascular stability and down-regulating proinflammatory cytokines such as TNF-α, IL-1β and IL-6. Results of studies described herein have indicated that administration of AM/AMBP-1 at 5 h after CLP maintained cardiac output, stroke volume, systemic oxygen delivery, and regional blood perfusion in the liver, gut, and kidneys at 20 h after the onset of sepsis. Similarly, post-onset treatment with AM/AMBP-1 attenuated liver damage and lactic acidosis, and prevented hemoconcentration at 20 h after CLP. Moreover, post-treatment with AM/AMBP-1 significantly decreased total peripheral vascular resistance under such conditions. Since administration of AM/AMBP-1 following the onset of sepsis maintains cardiovascular stability and attenuates tissue injury, these agents provide a novel approach to the treatment of sepsis. In addition, results also indicated that post-treatment with AM/AMBP-1 significantly down-regulated the production of TNF-α, IL-1β and IL-6 at 20 h after CLP. Although the precise mechanism responsible for the beneficial effect of AM/AMBP-1 in sepsis remains to be elucidated, the finding that the AM/AMBP-1 attenuates the up-regulation of TNF-α, IL-1β and IL-6 suggests a mechanism for these beneficial effects.

The amount of AM/AMBP-I administered will depend on the size and condition of the patient. Generally, the dosage of AM of 0.1 to 50 μg/kg body weight, including, for example, 0.2, 0.5, 1, 2, 5, 10, and 25 μg/kg, and AMBP-1 of 0.2 to 100 μg/kg body weight, including, for example, 0.5, 1, 2, 5, 10, 25, and 50 μg/kg, would be deemed appropriate, with the dosage on the low end of the dosage range being appropriate for the adult human. The compositions containing the active agents may be administered intravenously as a continuous drip. This is the most likely mode of administration, since these patients are hospitalized because of the gravity of their condition. The active agents are soluble, and would usually be administered in isotonic solutions such as Ringer's solution, buffered saline, etc. While liposomes may be prepared, such are usually not needed for protection when the agents are given by intravenous drip. However, the invention is not narrowly limited to any particular form of administration, and modes of administration other than continuous drip intravenous administration are within the scope of the invention.

The use of AM/AMBP-1 would be indicated for any vertebrate suffering from or likely to be exposed to sepsis. Other conditions when the AM/AMBP-1 might be particularly useful, either prophylactically or after onset of symptoms, include septic pregnancy or delivery, trauma or bacteremia.

While the AM and AMBP-1 may be given, it is also appropriate to administer the peptides having protective groups such as amides or ester groups attached thereto, since such protected peptides would be deprotected to deliver the AM and AMBP-1 in vivo. Because the peptides are water-soluble, it is possible to give them in aqueous solutions without addition of solubilizing agents.

The compositions containing the active agents may be administered before onset of sepsis (which has been shown to be beneficial in sepsis [Yang et al., 2002a]) when clear danger of sepsis is present, such as in instances when dirty wounds are suffered in an accident or military encounter.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

It was observed in studies in rats that AM (100 nM)/AMBP-1 (50 nM) reduced endotoxin (100 ng/ml)-stimulated release of TNF-α (Wu et al., 2003). This would suggest that AM may be an anti-inflammatory factor. In the current study, the significant rise in serum levels of TNF-α, IL-1β and IL-6 seen at 20 h after the onset of sepsis in the vehicle-treated animals was significantly blunted in the animals treated with AM/AMBP-1. In line with the beneficial effect of AM/AMBP-1 on the cardiovascular response, it is probable that down-regulation of proinflammatory cytokines by AM/AMBP-1 is one of the mechanisms responsible for the beneficial effects of these agents observed during sepsis. The plasma level of AM was found to be reduced at 20 h after CLP in animals treated with AM/AMBP-1 as compared with vehicle-treated animals. This apparently paradoxical result is explained by the fact that the available AM assay measures only unbound AM. Following administration of AM/AMBP-1, the fraction of unbound AM decreased due to an increase in AM bound to AMBP-1.

Materials and Methods

Animal Model of Polymicrobial Sepsis. Polymicrobial sepsis was induced by CLP in male adult Sprague-Dawley rats (300±12 g), Charles River Laboratories, Wilmington, Mass., as described previously (Wichterman et al., 1980). In brief, all experimental rats were fasted overnight but allowed water ad libitum prior to the experiment. Under anesthesia with isoflurane inhalation the cecum was exposed through a 2-cm abdominal midline incision, ligated just distal to the ileocecal valve in order to avoid intestinal obstruction, punctured twice with an 18-gauge needle, squeezed to expel a small amount of fecal material, and the abdominal incision was then closed in two layers. Sham-operated rats underwent the same procedure except that the cecum was neither ligated nor punctured. All animals received normal saline (3 ml/100 g body wt.) subcutaneously immediately after the surgery to provide fluid resuscitation. Various parameters were determined at 20 h after CLP [i.e., the late, hypodynamic phase of polymicrobial sepsis]. There were six animals in each group. The experiments described here were performed in adherence to the National Institutes of Health guidelines for the use of experimental animals. This project was approved by the Institutional Animal Care and Use Committee of the University of Alabama at Birmingham.

Administration of AM/AMBP-1. Synthetic rat AM (Phoenix Pharmaceuticals, Belmont, Calif.) and AMBP-1 (Cortex, San Leandro, Calif.) were co-administered via the femoral venous catheter using a Harvard Pump (Harvard Apparatus, Holliston, Mass.) at 5 h after CLP. Adrenomedullin (12 µg/kg body wt.) and AMBP-1 (40 µg/kg body wt.) were mixed in normal saline to a total volume of 1 ml which was infused over 1 h. This concentration of AM/AMBP-1 and infusion rate did not significantly alter mean arterial pressure (MAP) and heart rate (data not shown). Vehicle-treated animals received 1 ml of normal saline instead of AM/AMBP-1.

Determination of Cardiac Output and Organ Blood Flow. At 20 h after CLP or sham operation, cardiac output (CO) and regional blood flow were determined by using radioactive microspheres. In brief, both the right femoral artery and vein were cannulated with PE-50 tubing under isoflurane anesthesia. The catheter inserted into the femoral artery was connected to a blood pressure analyzer (Digi-Med, Louisville, Ky.) for the measurement of MAP and heart rate. An additional PE-50 catheter was inserted into the left ventricle via the right carotid artery. Strontium-85-labeled microspheres (DuPont/NEN, Boston, Mass.) were suspended in 15% dextran containing 0.05% Tween-80 surfactant to prevent aggregation and dispersed with a Vortex shaker for 3 min. An ~0.2 ml suspension, containing an estimated 150,000 microspheres with an activity of ~4 µCi was infused into the left ventricle over a period of 20 sec at a constant rate. The reference blood sample was withdrawn from the femoral arterial catheter beginning 20 sec before microsphere infusion and continuing for 80 sec at a rate of 0.7 ml/min. At the end of the experiment, the rats were euthanized with an overdose of pentobarbital sodium. Various organs/tissues were harvested, washed with normal saline, and gently blotted on filter paper. The radioactivity in the tissues, reference blood sample and the microspheres remaining in the syringe were counted on a Wallac automatic gamma counter (1480 Wizard, Wallac, Gaithersburg, Md.). CO, blood flow in various organs, stroke volume (SV) and total peripheral resistance (TPR) were calculated.

Determination of Systemic Oxygen Delivery and Hematocrit. Approximately 0.3 ml blood samples were withdrawn from the femoral artery and vein before the injection of microspheres. Oxygen content and hematocrit ($H_{sys}$) were measured using a blood gas analyzer (Radiometer Copenhagen, ABL 700 Series, Denmark). Systemic oxygen delivery ($DO_2$) and oxygen consumption ($VO_2$) were calculated by multiplying CO by arterial oxygen content or the difference between arterial and venous oxygen content, respectively.

Determination of Circulating Levels of Proinflammatory Cytokines. Two ml blood samples were collected in pyrogen/endotoxin free glass tubes at 20 h after CLP via cardiac puncture at least 2 min after the injection of radioactive microspheres. Please note that radioactivity in the collected blood samples was not significantly higher than the background levels. The blood samples were placed on ice for 10 min and centrifuged at 1,200 rpm for 10 min, serum samples were then stored at −70° C. until assayed. Serum levels of TNF-α, IL-1β and L-6 were measured using enzyme-linked immunosorbent assay kits (PharMingen, San Diego, Calif. for TNF-α, BioSource International, Camarillo, Calif. for IL-1β and IL-6) according to the manufacturer's instructions. The assay range was 0–1000 pg/ml for TNF-α, 0–2000 pg/ml for IL-1β, and 0–2000 pg/ml for IL-6. Please note that samples for IL-1β and IL-6 (not for TNF-α) were diluted by a factor of 1:2 prior to the assay.

Determination of Plasma Levels of Transaminases and Lactate. Additional 1.5 ml blood samples were collected in EDTA-coated test tubes at 20 h after CLP as described above. Plasma was separated immediately by centrifugation and stored at −70° C. until assayed. Plasma levels of alanine aminotransferase (ALT), aspartate aminotransferase (AST), and lactate were measured using Sigma kits (Sigma, St. Louis, Mo.) according to the manufacturer's instructions.

Determination of Plasma Levels of AM. At 20 h after CLP, a radioimmunoassay kit specific for rat AM (Peninsula Laboratories, Belmont, Calif.) was used to measure plasma levels of AM in various groups of animals according to the procedure provided by the manufacturer and described previously. Briefly, 1.0 ml blood samples were collected in polypropylene tubes containing EDTA (1 mg/ml) and aprotinin (500 KIU/ml). Plasma was separated immediately and stored at −70° C. until assayed. Adrenomedullin was extracted from 0.5 ml plasma on C18 columns eluted with 60% acetonitrile in 1% trifluoroacetic acid. Eluates were evaporated to dryness using a centrifugal concentrator. Samples were dissolved in RIA buffer and then incubated overnight at 4° C. with the antibody raised against rat AM. The [$^{125}$I]AM was then added for further overnight incubation at 4° C. Free and bound fraction of [$^{125}$I]AM were separated by the addition of a secondary antibody and centrifugation. Reactivity of the pellet was then measured. The rat AM assay does not have any cross-reactivity with human AM, amykin or endothelin-1.

Statistical Analysis. Data are presented as means±SE. One-way analysis of variance (ANOVA) and Tukey's test were employed for comparison among different groups of animals. The differences were considered significant at $p<0.05$.

Results

Effect of AM/AMBP-1 on Hemodynamic Parameters and Systemic Oxygen Delivery and Consumption. It was found that cardiac output (CO) and stroke volume (SV) decreased by 34% ($p<0.05$) and 42% ($p<0.05$), respectively, at 20 h after CLP with the administration of vehicle (normal saline). In contrast, total peripheral resistance (TPR) increased by 64% ($p<0.05$) under such conditions. Animals treated with AM/AMBP-1 at 5 h after CLP, however, had CO, SV and TPR value similar to sham-operated animals (no sepsis). In the AM/AMBP-1 treated group, CO was 43% higher (P<0.05) than the CO in vehicle-treated animals (Table 1). Similarly, at 20 h after CLP AM/AMBP-1-treated animals had systemic $DO_2$ value 35% higher (p<0.05) than the vehicle-treated group [which showed a 30% decrease (p<0.05) relative to the sham group] (Table 2). Moreover, AM/AMBP-1 prevented hemoconcentration at 20 h after CLP (Table 2). In contrast, systemic $VO_2$, MAP, and heart rate were not significantly altered with or without AM/AMBP-1 treatment (Table 2).

TABLE 1

Alterations in cardiac output (CO), stroke volume (SV) and total peripheral resistance (TPR) in septic animals treated with vehicle (normal saline) or AM/AMBP-1 as well as sham-operated animals and at 20 h after CLP.

|  | Sham | CLP + Vehicle | CLP + AM/AMBP-1 |
|---|---|---|---|
| CO (ml/min/100 g BW) | 25.98 ± 1.12 | 17.18 ± 0.98* | 24.56 ± 1.61# |
| SV (μl/beat/100 g BW) | 65.4 ± 4.3 | 38.0 ± 2.1* | 58.2 ± 4.9# |
| TPR (mmHg/ml/min/100 g BW) | 4.09 ± 0.24 | 6.68 ± 0.41* | 4.42 ± 0.25# |

There were six animals in each group. Data are expressed as means ± SE and compared by one-way ANOVA and Tukey's test:
*P < 0.0–01 vs. sham-operated animals;
P = 0.003 to 0.001 vs. CLP animals treated with vehicle.

TABLE 2

Alterations in hemodynamic parameters and systemic oxygen utilization at 20 hours after CLP.

|  | Sham | CLP + Vehicle | CLP + Am/AMBP-1 |
|---|---|---|---|
| Systemic $DO_2$ (ml/min/100 g BW) | 4.90 ± 0.22 | 3.45 ± 0.22* | 4.65 ± 0.25# |
| Systemic $VO_2$ (ml/min/100 g BW) | 0.97 ± 0.10 | 1.05 ± 0.12 | 1.23 ± 0.08 |
| MAP (mmHg) | 105 ± 2 | 113 ± 3 | 107 ± 1 |
| HR (beat/min) | 401 ± 14 | 453 ± 10 | 425 ± 9 |
| $H_{sys}$ | 43.7 ± 0.5 | 46.6 ± 0.9* | 44.3 ± 0.41# |

Values are presented as means ± SE (n = 6/group) and compared by one-way ANOVA and Tukey's test.
*P < 0.5 vs. the sham-operated animals;
P < 0.05 vs. the CLP animals treated with vehicle (normal saline).
AM, adrenomedullin;
AMBP-1, adrenomedullin binding protein.

Effect of AM/AMBP-1 on Regional Perfusion. As shown in Table 3, total hepatic blood flow in vehicle-treated animals decreased by 38% (P<0.05) at 20 h after CLP mainly as a result of a 42% decline (P<0.05) in the portal venous component without significant alteration in hepatic arterial blood flow. Administration of AM/AMBP-1, however, maintained hepatic perfusion at 20 h after CLP. Similarly, small intestinal and renal perfusion decreased by 54% (P<0.05) and 37% (P<0.05), respectively, at 20 h after CLP in vehicle-treated animals. Administration of AM/AMBP-1, however, prevented hypoperfusion in the gut and kidneys. Unlike the above organs, cardiac blood flow (i.e., coronary arterial blood flow) did not decrease at 20 h after CLP in vehicle-treated animals and AM/AMBP-1 did not significantly increase cardiac blood flow (Table 3).

TABLE 3

Alterations in regional blood flow at 20 hours after CLP.

|  | Sham | CLP + Vehicle | CLP + AM/AMBP-1 |
|---|---|---|---|
| Hepatic Arterial BF (ml/min/100 g tissue) | 27.0 ± 5.6 | 24.1 ± 3.6 | 32.5 ± 4.2 |
| Portal BF (ml/min/100 g tissue) | 155.7 ± 18.5 | 89.7 ± 15.4* | 167.0 ± 18.5# |
| Total Hepatic BF (ml/min/100 g tissue) | 182.7 ± 19.0 | 113.8 ± 16.2* | 199.5 ± 20.0# |
| Small Intestinal BF (ml/min/100 g tissue) | 188.9 ± 20.7 | 113.3 ± 18.6* | 285.7 ± 18.1*# |
| Renal BF (ml/min/100 g tissue) | 546.4 ± 22.9 | 393.4 ± 24.5* | 558.2 ± 8.6# |
| Cardiac BF (ml/min/100 g tissue) | 727.2 ± 144.0 | 452.1 ± 64.9 | 671.9 ± 139.9 |

Values are represented as means ± SE (n = 6/group) and compared by one-way ANOVA and Tukey's test.
*P < 0.5 vs. the sham-operated animals;
P < 0.05 vs. the CLP animals treated with vehicle (normal saline).
AM, adrenomedullin;
AMBP-1, adrenomedullin binding protein-1;
BF, blood flow.

Effect of AM/AMBP-1 on Circulating Levels of Proinflammatory Cytokines. It was found that serum levels of TNF-α, IL-1β and IL-6 increased by 12, 15 and 7 fold, respectively, at 20 h after CLP in vehicle-treated animals. Administration of AM/AMBP-1, however, significantly reduced serum levels of TNF-α, IL-1β, and IL-6 at 20 h after CLP. In contrast, administration of AM/AMBP-1 did not alter circulating levels of these cytokines in sham-operated animals (Table 4).

TABLE 4

Alterations in serum TNF-α, IL-1β and IL-6 in septic animals treated with vehicle (normal saline) or AM/AMBP-1, as well as sham-operated animals at 20 hours after CLP.

|  | Sham | CLP + Vehicle | CLP + AM/AMBP-1 |
|---|---|---|---|
| TNF-α (pg/ml) | 20.5 ± 8.4 | 273.2 ± 61.8* | 46.9 ± 12.7# |
| IL-1β (pg/ml) | 11.4 ± 3.9 | 183.9 ± 58.1* | 43.5 ± 12.7# |
| IL-6 (pg/ml) | 274.5 ± 16.4 | 2317.8 ± 310.4* | 1314.9 ± 186.6*# |

There were six animals in each group. Data are expressed as means ± SE (n = 6/group) and compared by one-way ANOVA and Tukey's test:
*P = 0.008 to 0.001 vs. the sham-operated animals;
P = 0.029 to 0.002 vs. the CLP animals treated with vehicle.

Effect of AM/AMBP-1 on Plasma Levels of Transaminases and Lactate. It was found that plasma levels of ALT and AST increased by 3.2 and 2.4 fold, respectively, at 20 h after CLP in vehicle-treated animals (p<0.05). Administration of AM/AMBP-1, however, reduced the extent of ALT and AST elevation by 46% and 52% (p<0.05), respectively, as compared to vehicle-treated animals. ALT and AST levels in septic animals treated with AM/AMBP-1 and in sham-operated animals were not statistically different. Similarly, circulating levels of lactate increased by 168% (P<0.05) at 20 h after CLP in vehicle-treated animals, however, administration of AM/AMBP-1 attenuated the increase in lactate (P<0.05) (Table 5).

TABLE 5

Alterations in plasma levels of alanine aminotransferase (ALT), aspartate aminotransferase (AST) and plasma levels of lactate in septic animals treated with vehicle (normal saline) or AM/AMBP-1, as well as sham-operated animals at 20 hours after CLP.

|  | Sham | CLP + Vehicle | CLP + AM/AMBP-1 |
| --- | --- | --- | --- |
| ALT (SF U/ml) | 20.0 ± 2.0 | 83.7 ± 9.3* | 44.7 ± 3.4# |
| AST (SF U/ml) | 48.8 ± 3.4 | 168.0 ± 16.9* | 81.0 ± 7.6# |
| Lactate (mg/dl) | 18.5 ± 2.2 | 51.0 ± 4.2* | 27.0 ± 2.9# |

There were six animals in each group. Data are expressed as means ± SE and compared by one-way ANOVA and Tukey's test:
*$P < 0.001$ vs. the sham-operated animals;
$P < 0.001$ vs. the CLP animals treated with vehicle.

Effect of AM/AMBP-1 on Plasma Levels of AM at 20 h after CLP. It was found that plasma levels of AM increased by 146% at 20 h after CLP in vehicle-treated animals ($P<0.05$). The plasma levels of AM in AM/AMBP-1-treated animals showed a statistically insignificant rise compared to the sham group, but it was significantly lower than the AM level in vehicle-treated group (Table 6).

TABLE 6

Alterations in plasma levels of AM in septic animals treated with vehicle (normal saline) or AM/AMBP-1, as well as sham-operated animals at 20 hours after CLP.

|  | Sham | CLP + Vehicle | CLP + AM/AMBP-1 |
| --- | --- | --- | --- |
| Plasma AM Levels (pg/ml) | 173 ± 14 | 426 ± 31* | 257 ± 19*# |

There were six animals in each group. Data are expressed as means ± SE and compared by one-way ANOVA and Tukey's test.
*$P < 0.001$ vs. the sham-operated animals;
$P < 0.001$ vs. the CLP animals treated with vehicle.

Administration of AM/AMBP-1 Simultaneously with the Initiation of Sepsis. Synthetic rat AM (Phoenix Pharmaceuticals, Belmont, Calif.) was administered continuously via a jugular vein using an Alzet mini-osmotic pump (Durect, Cupertino, Calif.) for the entire duration of the study. Rats were fasted overnight but allowed water ad libitum prior to the experiment. The fasted animals were anesthetized with isoflurane inhalation and a 1.0 cm incision was made in the neck. A 200 µl mini-osmotic pump was prefilled with AM solution (dissolved with sterile normal saline to 20 µg/ml) and connected to a silastic catheter (size 0.030" I.D., 0.065" O.D., Baxter, McGaw Park, Ill.). The prefilled pump was then primed in sterile normal saline for 2 h at 37° C. before implantation. The prefilled and primed mini-osmotic pump was then implanted subcutaneously in the rat 3 h prior to induction of sepsis and the silastic catheter was inserted into the right jugular vein for continuous infusion of AM at a constant rate of 8 µl/h for 23 h (total dosage 12 µg/kg body wt). Following the close of the neck incision, CLP was performed 3 h after the implantation of the pump. The right femoral vein was then cannulated using PE-50 tubing and 1 ml human AMBP-1 solution (containing 12 µg AMBP-1, Cortex, San Leandro, Calif.) was infused via the femoral venous catheter using a Harvard Pump (Harvard Apparatus, Holliston, Mass.) at a rate of 0.05 ml/min for a period of 20 min. The dose of AMBP-1 administered was approximately 40 µg/kg body wt. Vehicle-treated animals received sterile normal saline instead of AM/AMBP-1. In additional groups of septic animals, either AM alone (12 µg/kg body wt.) or AMBP-1 alone (40 µg/kg body wt.) was administered, as described above, in order to determine the effect of each individual agent on septic cardiovascular responses. It should be noted that AM at a dose of 12 µg/kg body wt. was used since it increases plasma AM to a level which at least doubles AM concentration observed during sepsis (600–700 pg/ml at 10–20 h after CLP). The dosage of AMBP-1 used in this study was based the preliminary study in which $2-5 \times 10^{-9}$ M AMBP-1 significantly enhanced AM-induced vascular relaxation.

Effects of AM/AMBP-1 on the Survival Rate. The survival rate after CLP and cecal excision with vehicle administration was 57% at days 2–6 and decreased to 43% at days 7–10. Administration of AM/AMBP-1 at 5 h after CLP, however, reduced the mortality rate to 7% at days 7–10 ($P<0.05$ on day 10) (Table 7). The results also show that, when administered simultaneously with exposure to sepsis, AM/AMBP-1 improved CO, $DO_2$, organ blood flow, and reduces TPR, ALT, AST and lactate at 20 h after CLP (data not shown).

TABLE 7

Effects of AM/AMBP-1 on the survival rate (%) at 10 days after cecal ligation and puncture and cecal excision with vehicle treatment (CLPE + Vehicle) and cecal ligation and puncture with AM/AMBP-1 treatment (CLPE + AM/AMBP-1).

| Days after CLPE | 1 | 2 | 3 | 4 | 5 | 6 | 7 | 8 | 9 | 10 |
| --- | --- | --- | --- | --- | --- | --- | --- | --- | --- | --- |
| CLPE + Vehicle | 85.7 | 57.1 | 57.1 | 57.1 | 57.1 | 57.1 | 42.9 | 42.9 | 42.9 | 42.9 |
| CLPE + AM/AMBP-1 | 100 | 100 | 100 | 100 | 100 | 100 | 92.9 | 92.9 | 92.9 | 92.9 |

There were 14 animals in each group, and the data were analyzed by the Kaplan-Meier method and compared by the logrank test. $P < 0.05$ vs. CLPE + Vehicle.

The above data and other supporting data are also found in Yang et al., 2002a; Yang et al., 2002b; and Wu et al., 2000, the contents of which are incorporated in their entirety by reference.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of attenuating organ damage due to shock in a patient who is suffering sepsis or is likely to suffer sepsis, the method comprising administering to the patient amounts of adrenomedullin and adrenomedullin binding protein-1 effective to attenuate organ damage in the patient.

2. The method of claim 1 wherein the adrenomedullin and adrenomedullin binding protein-1 are administered as one single composition.

3. The method of claim 2 wherein said composition is administered before onset of sepsis.

4. The method of claim 2 wherein the composition is administered during the hyperdynamic phase of sepsis.

5. A composition comprising, adrenomedullin and adrenomedullin binding protein-1 in amounts effective to prevent organ damage in a patient due to shock.

6. The method of claim 1, wherein the adrenomedullin or the adrenomedullin binding protein-1, or both, further comprises a protective group that is deprotected after administration to the patient.

7. The method of claim 6, wherein the protective group is an amide or ester group.

8. The composition of claim 5, wherein the adrenomedullin or the adrenomedullin binding protein-1, or both, further comprises a protective group that is deprotected when the composition is administered to a patient.

9. The composition of claim 8, wherein the protective group is an amide or ester group.

* * * * *

UNITED STATES PATENT AND TRADEMARK OFFICE
CERTIFICATE OF CORRECTION

| | | |
|---|---|---|
| PATENT NO. | : 6,864,237 B2 | Page 1 of 1 |
| APPLICATION NO. | : 10/439762 | |
| DATED | : March 8, 2005 | |
| INVENTOR(S) | : Ping Wang | |

It is certified that error appears in the above-identified patent and that said Letters Patent is hereby corrected as shown below:

In Column 1, lines 11-16,

"STATEMENT REGARDING FEDERALLY SPONSORED RESEARCH OR DEVELOPMENT

The research from which this invention resulted was supported by the United States Government, National Institutes of Health, grants RO1 GM57468 and KO2 A101461."

should read

--STATEMENT OF GOVERNMENT SUPPORT

This invention was made with government support under grants GM57468 and KO2 A101461 awarded by the National Institutes of Health. The government has certain rights in the invention.--

Signed and Sealed this
Sixteenth Day of August, 2011

David J. Kappos
*Director of the United States Patent and Trademark Office*